United States Patent
Machida (10) Patent No.: US 9,675,326 B2
(45) Date of Patent: Jun. 13, 2017

(54) IMAGE RECONSTRUCTING APPARATUS, IMAGE RECONSTRUCTING METHOD, AND NON-TRANSITORY COMPUTER-READABLE STORAGE MEDIUM

(71) Applicant: CANON KABUSHIKI KAISHA, Tokyo (JP)

(72) Inventor: Yoshihito Machida, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 14/969,532

(22) Filed: Dec. 15, 2015

(65) Prior Publication Data
US 2016/0179346 A1 Jun. 23, 2016

(30) Foreign Application Priority Data
Dec. 22, 2014 (JP) ................. 2014-259276

(51) Int. Cl.
*A61B 8/08* (2006.01)
*A61B 5/00* (2006.01)
(Continued)

(52) U.S. Cl.
CPC .......... *A61B 8/5207* (2013.01); *A61B 5/0073* (2013.01); *G06K 9/00798* (2013.01);
(Continued)

(58) Field of Classification Search
CPC ....... G06T 7/0012; G06T 7/0016; G06T 7/55; G06T 2207/10124; G06T 2207/20092;
(Continued)

(56) References Cited

U.S. PATENT DOCUMENTS 5,359,638 A * 10/1994 Hsieh .................. G06T 11/005
 250/252.1
5,469,487 A * 11/1995 Hu ........................ A61B 6/032
 378/15
(Continued)

FOREIGN PATENT DOCUMENTS

JP 2006-025868 A 2/2006
WO WO 2012106460 A2 * 8/2012 ........... G06T 11/006

OTHER PUBLICATIONS

"Handbook of Medical Imaging, Medical Imaging Technology", The Japanese Society of Medical Imaging Technology, Sep. 15, 2012, Editorial Committee of Handbook of the Japanese Society of Medical Imaging Technology, Japan.
(Continued)

*Primary Examiner* — Manav Seth
(74) *Attorney, Agent, or Firm* — Fitzpatrick, Cella, Harper & Scinto (57) ABSTRACT

An image reconstructing apparatus creates a reconstructed image for every calculation operation by performing predetermined repetitive calculation by iterative reconstruction for a plurality of images obtained by acquiring an object from different angles, extracts at least one reconstructed image under a predetermined condition from the created reconstructed images, displays on a display unit information corresponding to the extracted reconstructed images and information corresponding to the extracted reconstructed image, selects at least one reconstructed image in accordance with an instruction of an operator on the display unit, and outputs the selected reconstructed image.

13 Claims, 8 Drawing Sheets

(51) Int. Cl.
*G06K 9/00* (2006.01)
*G06T 7/00* (2017.01)
*G06T 7/55* (2017.01)

(52) U.S. Cl.
CPC ........ *G06K 9/00818* (2013.01); *G06T 7/0012* (2013.01); *G06T 7/55* (2017.01); *G06T 2207/10124* (2013.01); *G06T 2207/20092* (2013.01); *G06T 2207/30168* (2013.01); *G06T 2211/416* (2013.01); *G06T 2211/421* (2013.01)

(58) Field of Classification Search
CPC . G06T 2207/20108; G06T 2207/20221; G06T 2207/30168; G06T 2211/416; G06T 2211/421; G06K 9/00798; G06K 9/00818; A61B 5/0073; A61B 8/5207
See application file for complete search history.

(56) References Cited

U.S. PATENT DOCUMENTS

| | | | | |
|---|---|---|---|---|
| 6,426,988 B2 * | 7/2002 | Yamada | ................ | G06T 11/005 378/4 |
| 6,795,522 B2 * | 9/2004 | Nishide | ................ | G06T 11/005 378/19 |
| 6,987,829 B2 * | 1/2006 | Claus | .................... | G06T 11/006 378/22 |
| 7,023,951 B2 * | 4/2006 | Man | ......................... | A61B 6/00 378/4 |
| 7,447,295 B2 * | 11/2008 | Hoheisel | ................ | A61B 6/032 378/4 |
| 7,596,202 B2 * | 9/2009 | Nielsen | ................ | G06T 11/006 378/4 |
| 7,646,902 B2 * | 1/2010 | Chan | ...................... | G06K 9/00 382/128 |
| 7,672,421 B2 * | 3/2010 | Chen | ..................... | G06T 11/005 378/4 |
| 8,121,378 B2 * | 2/2012 | George | ................. | G06T 11/006 378/21 |
| 8,218,715 B2 * | 7/2012 | Sauer | ..................... | A61B 6/032 378/207 |
| 8,897,535 B2 * | 11/2014 | Ruth | ..................... | G06T 11/006 382/128 |
| 2002/0177773 A1 * | 11/2002 | Natterer | .................. | G06T 17/20 600/436 |
| 2004/0264625 A1 * | 12/2004 | Basu | ...................... | A61B 6/032 378/4 |
| 2005/0105693 A1 * | 5/2005 | Zhao | ..................... | G06T 11/006 378/210 |
| 2016/0151035 A1 * | 6/2016 | Noda | ..................... | A61B 6/032 378/26 |

OTHER PUBLICATIONS

Yoshihito Machida, U.S. Appl. No. 14/958,933, filed Dec. 3, 2015.

* cited by examiner

IMAGE RECONSTRUCTING APPARATUS, IMAGE RECONSTRUCTING METHOD, AND NON-TRANSITORY COMPUTER-READABLE STORAGE MEDIUM

BACKGROUND OF THE INVENTION

Field of the Invention

The present invention relates to an image reconstructing apparatus, an image constructing method, and a non-transitory computer-readable storage medium and, more particularly, to a technique of outputting the image quality of an image obtained by iterative reconstruction.

Description of the Related Art

An imaging apparatus acquires a plurality of images from different angles, and creates a reconstructed image from these images using a technique called an image reconstructing method. As image reconstructing methods, methods called a filtered back projection method and iterative reconstruction have been described in the Handbook of Medical Imaging, Medical Imaging Technology, in 2012.

Among others, the iterative reconstruction is an image reconstructing method of performing calculation by repeating forward projection for calculating a projected image from a reconstructed image obtained by back projection (to be described later) and back projection for calculating a reconstructed image from the projected image. This reconstructing method calculates a coefficient by comparing the projected image obtained from the reconstructed image with an image acquired by an imaging apparatus, and performs back projection using the coefficient. Therefore, the image quality of a reconstructed image changes every time calculation is repeated. In this reconstructing method, it is expected to obtain the effect of obtaining a less noisy image while maintaining the sharpness. However, if repetitive calculation is excessively performed, an attempt to reproduce noise in a acquired image is made, thereby unwantedly increasing noise.

Japanese Patent Laid-Open No. 2006-25868 describes a method in which when performing reconstruction by iterative reconstruction, a region of interest is set on a reconstructed image as an intermediate result, and it is determined based on the standard deviation of the region whether to further perform calculation.

There are various applications and purposes of reconstructed images, which require different image qualities. It is, therefore, necessary to construct a system that can satisfy the requirements.

SUMMARY OF THE INVENTION

According to one aspect of the present invention, there is provided an image reconstructing apparatus which comprises a creation unit configured to create a reconstructed image for every calculation operation by performing predetermined repetitive calculation by iterative reconstruction for a plurality of images obtained by acquiring an object from different angles; an extraction unit configured to extract at least one reconstructed image under a predetermined condition from the reconstructed images created by the creation unit; a selection unit configured to display on a display unit information corresponding to the reconstructed images extracted by the extraction unit and information corresponding to the extracted reconstructed image, and to select at least one reconstructed image in accordance with an instruction of an operator on the display unit; and an output unit configured to output the at least one reconstructed image selected by the selection unit.

Further features of the present invention will become apparent from the following description of exemplary embodiments (with reference to the attached drawings).

DESCRIPTION OF THE EMBODIMENTS

First Embodiment

Figure 1:
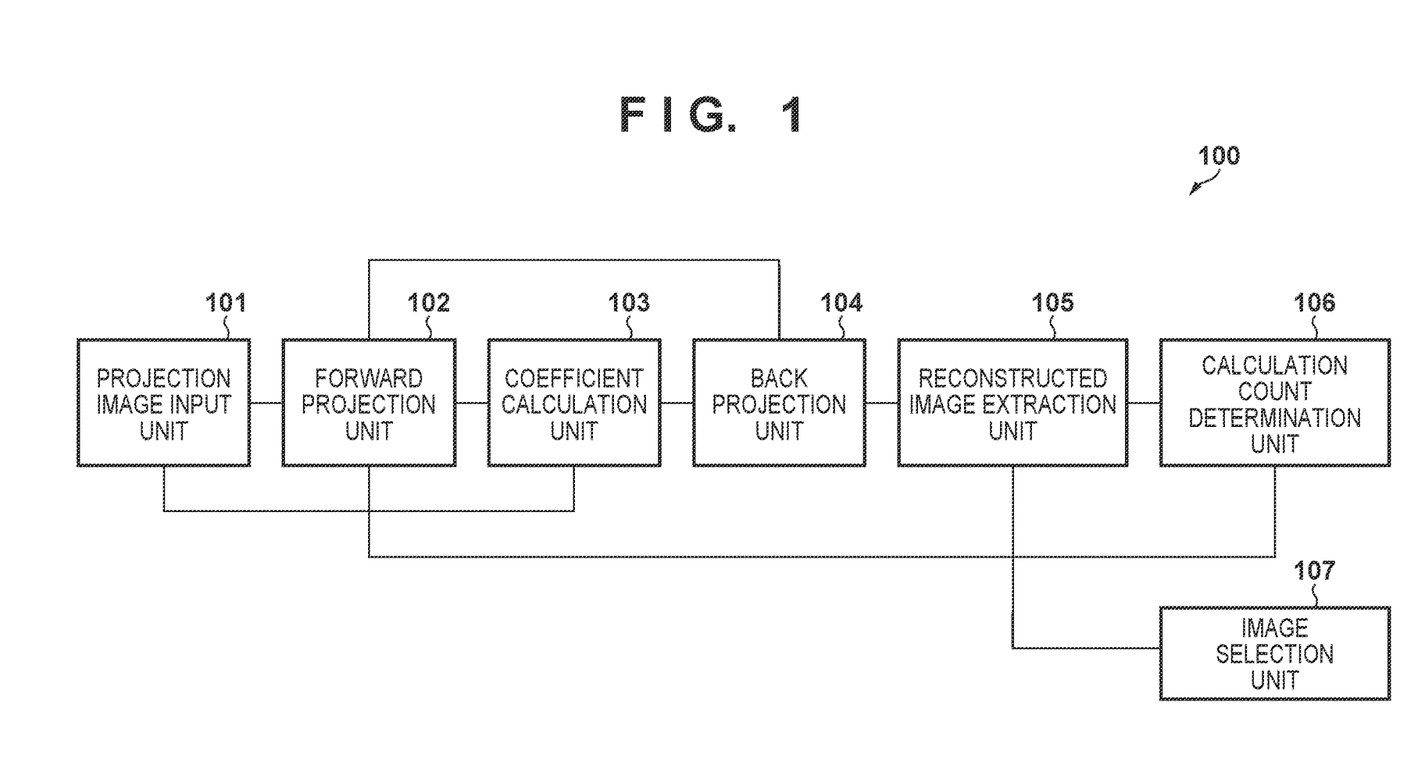
FIG. 1 is a block diagram showing the arrangement of an image reconstructing apparatus 100.

An image reconstructing apparatus 100 according to the first embodiment will be described with reference to FIGS. 1 to 4. FIG. 1 is a block diagram showing the arrangement of the image reconstructing apparatus 100 according to this embodiment. As shown in FIG. 1, the image reconstructing apparatus according to this embodiment includes a projection image input unit 101, a forward projection unit 102, a coefficient calculation unit 103, a back projection unit 104, a reconstructed image extraction unit 105, a calculation count determination unit 106, and an image selection unit 107.

Figure 2:
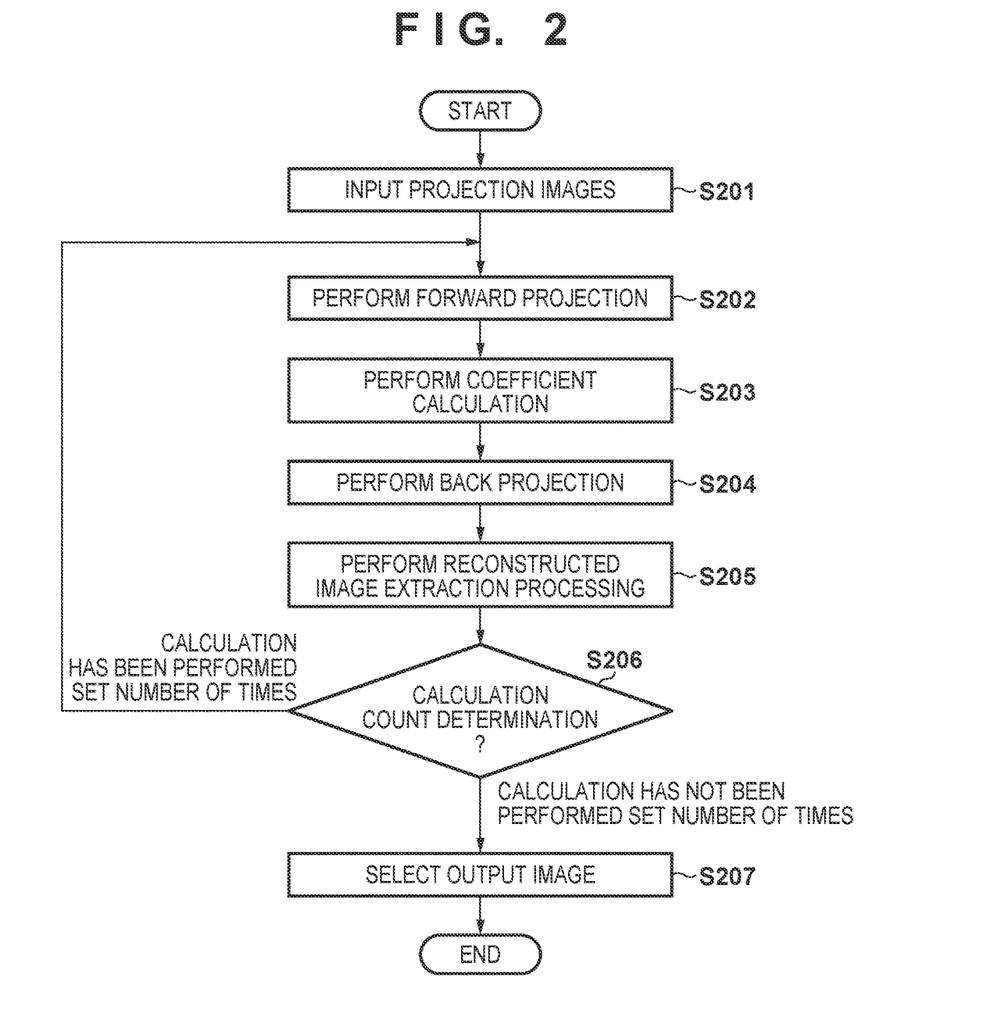
FIG. 2 is a flowchart illustrating a processing procedure executed by the image reconstructing apparatus 100.

The operation of the above-described image reconstructing apparatus 100 will be described with reference to FIG. 2. FIG. 2 is a flowchart illustrating a processing procedure executed by the image reconstructing apparatus 100. In step S201, the projection image input unit 101 receives, as inputs, a plurality of images (to be referred to as projection images hereinafter) acquired by an imaging unit (not shown) from different angles, and outputs them to the coefficient calculation unit 103. Steps S202 to S205 correspond to a reconstructed image creation process by iterative reconstruction. In step S202, the forward projection unit 102 receives, as an input, a reconstructed image output from the back projection unit 104, and creates a forward projection image. Note that if the calculation count is one, a reconstructed image containing an appropriate value other than 0 is input to the forward projection unit 102.

In step S203, the coefficient calculation unit 103 compares the forward projection image with the projection image, thereby performing coefficient calculation. In step S204, the back projection unit 104 creates and updates the reconstructed image based on the reconstructed image and a coefficient. In step S205, the reconstructed image extraction unit 105 extracts one or more reconstructed images from the created reconstructed images under a predetermined condition, and outputs the extracted reconstructed images to the image selection unit 107. At this time, the images extracted and output from the reconstructed image extraction unit 105 are all saved in the image selection unit 107. Note that in this embodiment, the reconstructed image extraction unit 105 extracts the created reconstructed image every time repetitive calculation is performed.

In step S206, the calculation count determination unit 106 determines whether calculation has been performed a set number of times. If the calculation has not been performed the set number of times, the reconstructed image created by the back projection unit 104 is output to the forward projection unit 102, and the process returns to step S202. If it is determined in step S206 that the calculation has been performed the number of times, the process advances to step S207. Note that the above-described the number of times of calculation indicates the repetition count of steps S202 to S204. In step S207, the image selection unit 107 selects the reconstructed image requested by an operator, and outputs the selected reconstructed image. The operation of the image selection unit 107 will be described in detail later. By performing the processes in steps S201 to S207, the operator can acquire the reconstructed image according to a purpose and application from the reconstructed images.

Figure 3:
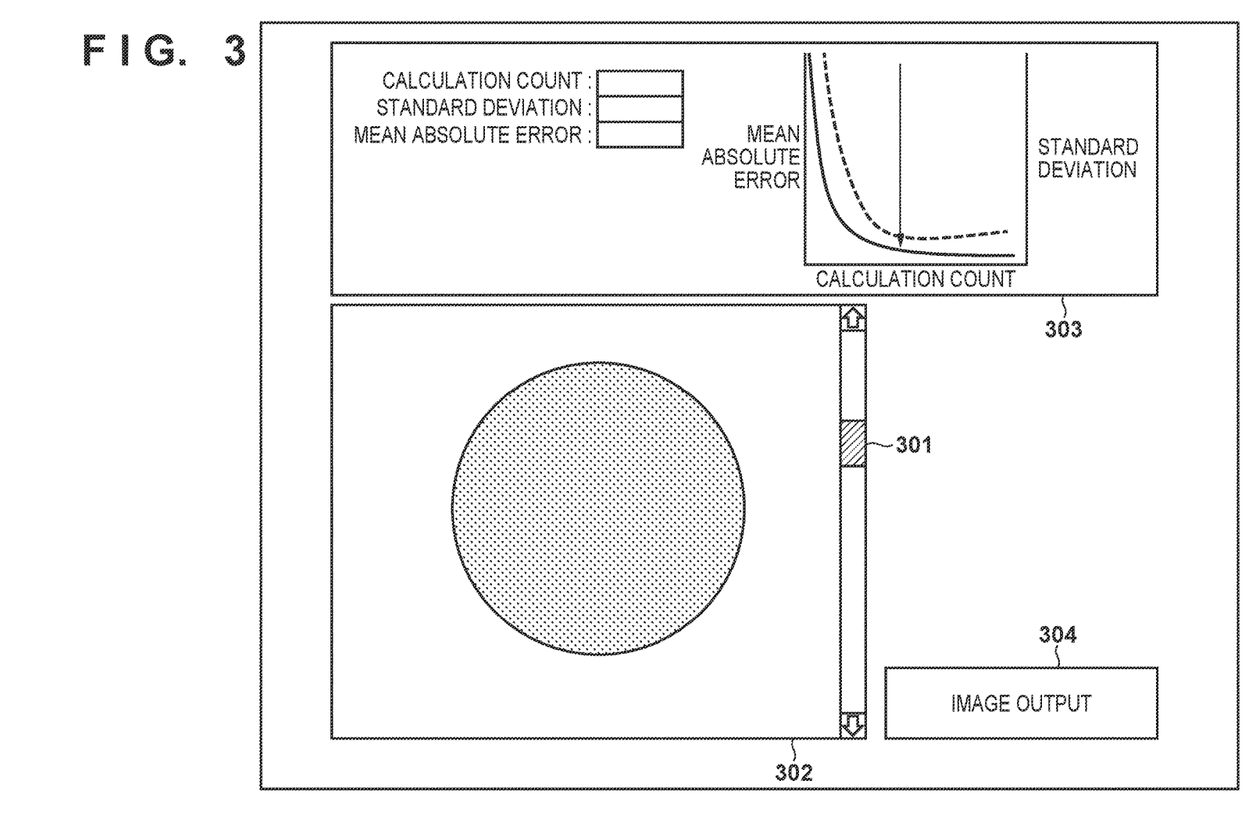
FIG. 3 is a schematic view showing an example of an image selection unit 107.
Figure 4:
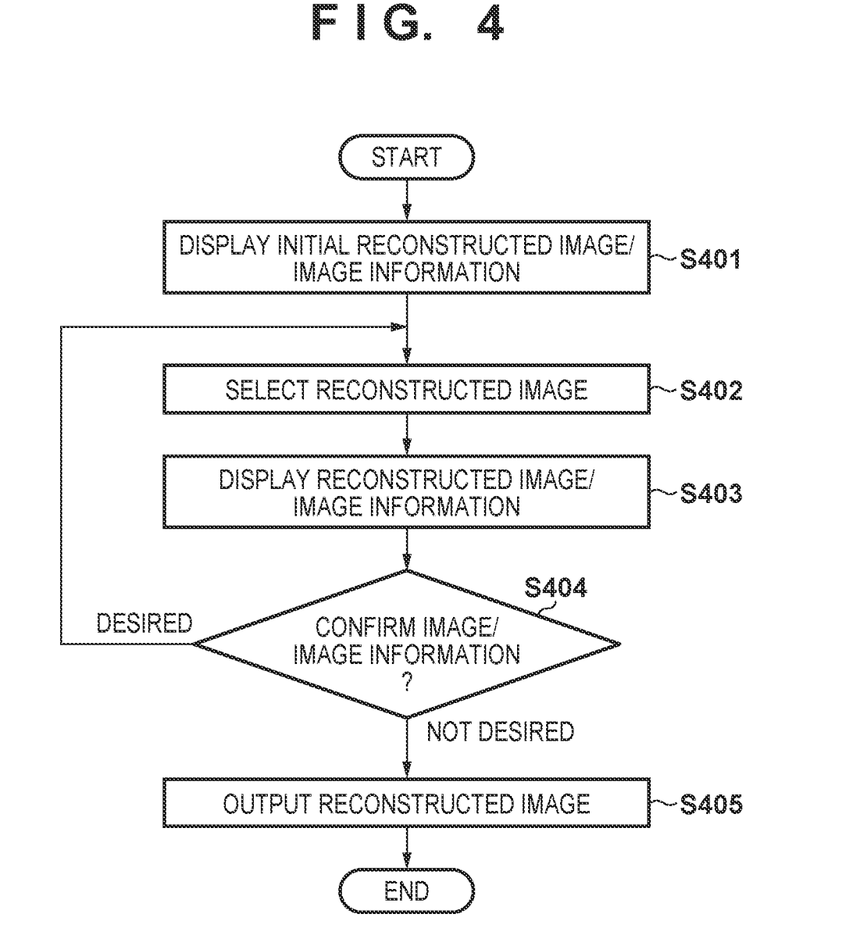
FIG. 4 is a flowchart illustrating a processing procedure executed by the image selection unit 107.

The operation of the image selection unit 107 for selecting and outputting, by the operator, the extracted reconstructed image will be described with reference to FIGS. 3 and 4. The arrangement of the image selection unit 107 will be described with reference to FIG. 3. FIG. 3 is a schematic view showing an example of the image selection unit 107 according to this embodiment. The image selection unit 107 is constituted by display units for displaying various kinds of information, and includes an image selection instruction unit 301, an image display unit 302, a reconstruction information display unit 303, and an image output instruction unit 304.

The image selection instruction unit 301 serves as a user interface used by the operator to select and instruct one of the reconstructed images output from the reconstructed image extraction unit 105. The image selection instruction unit 301 according to this embodiment is formed from two arrow buttons and a slide bar. When the operator presses the up arrow button, the image selection instruction unit 301 selects the reconstructed image with a smaller calculation count among the reconstructed images. When the operator presses the down arrow button, the image selection instruction unit 301 selects the reconstructed image with a larger calculation count among the reconstructed images. In addition, when the operator performs an operation of moving the slide bar upward, the image selection instruction unit 301 selects the reconstructed image with a smaller calculation count among the reconstructed images. When the operator performs an operation of moving the slide bar downward, the image selection instruction unit 301 selects the reconstructed image with a larger calculation count among the reconstructed images.

Note that the image selection instruction unit 301 according to this embodiment need only be able to select and instruct one of the plurality of reconstructed images. Any arrangement may be adopted. For example, the arrow buttons and slide bar may be arranged in the horizontal direction, or a calculation count may be directly input. A button for switching the selected image for every predetermined time when it is pressed may be added as the image selection instruction unit 301. By adding such button, the operator can sequentially select the plurality of reconstructed images by performing one operation.

The image display unit 302 displays the reconstructed image selected by the image selection instruction unit 301. The image display unit 302 accepts an operation of changing the contrast and luminance of the image, enlarged/reduced display, or the like, and performs contrast and luminance adjustment, display magnification adjustment, slice position adjustment, slice selection, or the like in accordance with an operator instruction. Note that the number of images displayed on the image display unit 302 is one in this embodiment. However, the image display unit 302 may simultaneously display a plurality of images corresponding to difference slice sections or slice directions. This allows the operator to readily select the reconstructed images.

The reconstruction information display unit 303 displays additional information (reconstruction information) corresponding to the reconstructed image selected by the image selection instruction unit 301. The reconstruction information may contain a calculation count corresponding to the selected reconstructed image. In addition, the reconstruction information may contain, as the feature values of the selected reconstructed image, the standard deviation of the pixel values of the reconstructed image, and the average value (to be referred to as a mean absolute error hereinafter) of the absolute values of differences between the pixels of the projection image (the image before calculation) and those of the forward projection image obtained at a reconstructed image creation stage. Note that the reconstruction information is not limited to them.

The reconstruction information display unit 303 according to this embodiment displays a graph showing the relationship between the pieces of reconstruction information, for example, a graph showing the relationship between the calculation count, the mean absolute error, and the standard deviation. The reconstruction information display unit 303 according to this embodiment adds an arrow mark on the graph showing the relationship between the calculation count, the mean absolute error, and the standard deviation so as to readily determine the calculation count of the image displayed on the image display unit 302. By displaying the reconstruction information in addition to the reconstructed image, the operator can select an output image using not only the information of the reconstructed image but also information around the reconstructed image.

The image output instruction unit 304 serves as a user interface used by the operator to output and instruct the reconstructed image selected by the image selection instruction unit 301.

An example of processing performed using the above-described image selection unit 107 will be described with reference to FIG. 4. FIG. 4 is a flowchart illustrating a processing procedure executed by the image selection unit 107 according to this embodiment. In step S401, the image display unit 302 and reconstruction information display unit 303 display the image extracted/output last from the reconstructed image extraction unit 105, and its reconstruction information, respectively. In step S402, the operator selects the reconstructed image using the image selection instruction unit 301. In step S403, the image display unit 302 and reconstruction information display unit 303 display the selected reconstructed image and its reconstruction information, respectively. Furthermore, if the operator issues a contrast, luminance, or magnification adjustment instruction or the like, the image display unit 302 displays the image in accordance with the instruction.

In step S404, the operator confirms the image and information respectively displayed on the image display unit 302 and reconstruction information display unit 303. If the image and information are desired ones, the process advances to step S405. If the operator determines that the displayed image is not a desired one, the process returns to step S402. In step S405, the operator outputs the reconstructed image using the image output instruction unit 304.

By performing the processes in steps S401 to S405, the operator can select and output the desired image from the extracted reconstructed images. Furthermore, in this embodiment, when the reconstruction information of the reconstructed image is displayed in addition to the image, quantitative image evaluation is possible, and the operator readily selects the desired image.

[First Modification]

In this embodiment, the arrangement of extracting the reconstructed image every time repetitive calculation is performed is adopted. However, the reconstructed image may be extracted for every predetermined number of times of repetitive calculation. For example, an arrangement of extracting an image for every predetermined number of times of repetitive calculation, for example, for every 10 times of repetitive calculation, an arrangement of extracting/outputting images at predetermined timings, for example, extracting images at the 10th, 20th, 40th, and 80th calculation operations, or the like may be adopted. This can reduce the number of selection candidate reconstructed images, and the operator can thus efficiently select the reconstructed image.

[Second Modification]

In this embodiment, the arrangement of extracting the reconstructed image every time repetitive calculation is performed is adopted. However, the reconstructed image may be extracted for each of other pieces of reconstruction information. For example, an arrangement of extracting an image for each change amount in predetermined coefficient, an arrangement of extracting an image for each change amount in standard deviation of the pixel values of a predetermined image, or the like may be adopted. This can narrow down the selection candidates reconstructed images, and the operator can thus efficiently select the reconstructed image.

[Third Modification]

In this embodiment, the number of reconstructed images to be selected and output is one. However, a plurality of reconstructed images may be output in accordance with a predetermined application. With this operation, if a high-contrast image of calcification or the like whose X-ray absorptance is relatively high and a low-contrast image of a tumor or the like whose X-ray absorptance is relative low are required, the operator can efficiently select both the images.

[Fourth Modification]

Figure 5:
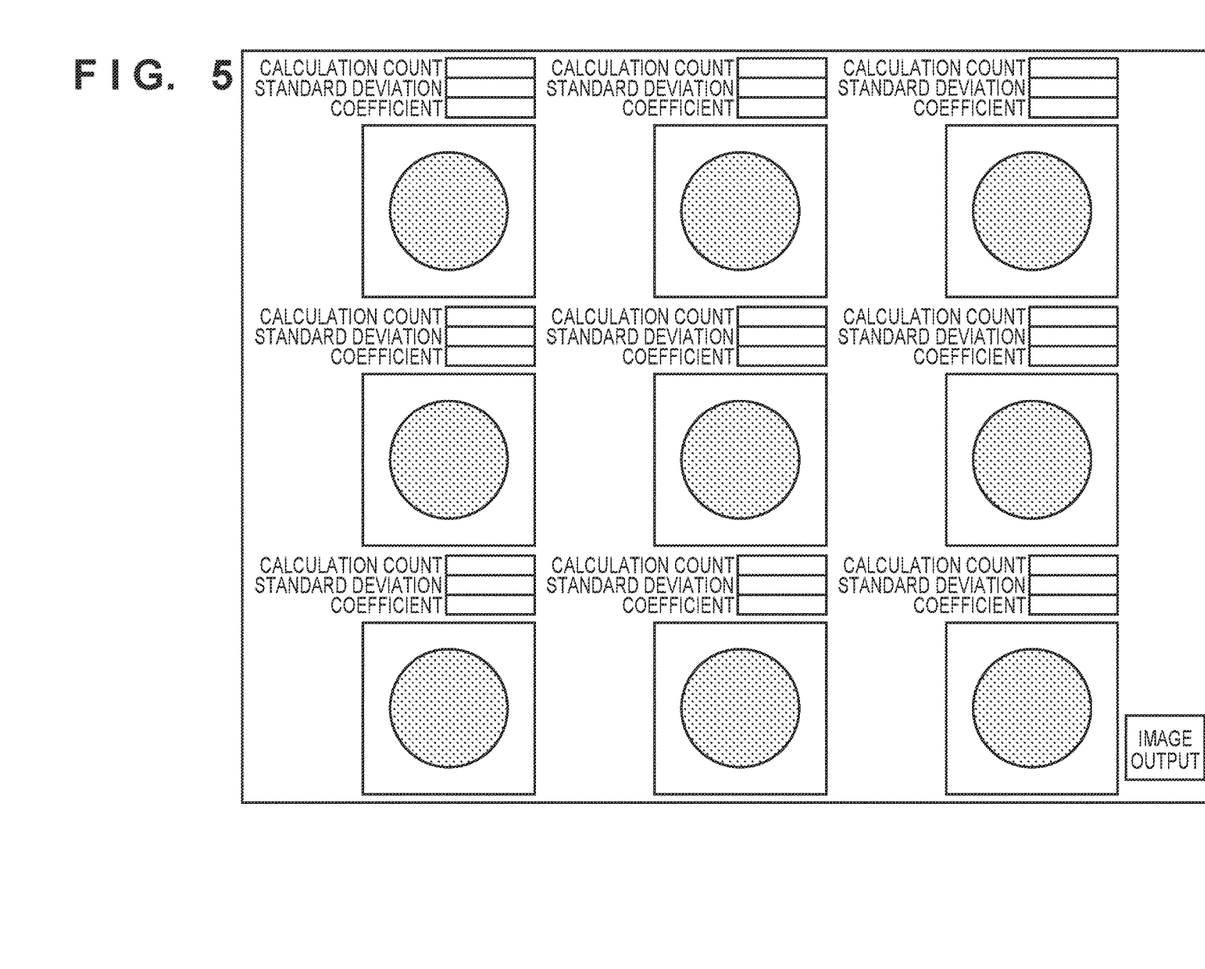
FIG. 5 is a schematic view showing an example of the image selection unit 107.

In this embodiment, the arrangement of displaying, on the image display unit 302, the image selected and instructed by the image selection instruction unit 301 is adopted. However, the present invention is not limited to this. FIG. 5 is a schematic view showing an example of display of the image selection unit 107 according to the fourth modification. An arrangement may be adopted in which a plurality of reconstructed images with different calculation counts are displayed on the image display unit 302, and directly selected, as shown in FIG. 5. This can facilitate an image selection operation, and the operator can thus efficiently select the reconstructed image.

[Fifth Modification]

In this embodiment, an arrangement of selecting the reconstructed image after calculation is performed the preset number of times is adopted. However, an operation of sequentially displaying the images on the image selection unit 107, and terminating repetitive calculation when an image output instruction is issued may be performed. This can interrupt the processing when the reconstructed image requested by the operator is output, and the operator can thus efficiently acquire the reconstructed image.

[Sixth Modification]

In this embodiment, an arrangement of displaying the feature values of the pixel values of the reconstructed image is adopted. However, the feature values of pixels values in a region of interest (a specific range) may be displayed in the reconstructed image. For example, the operator may designate a region of interest in the reconstructed image, and calculate and display a standard deviation in the region of interest. If the reconstructed images are sequentially displayed as in the fifth modification, a unit of designating a region of interest may be provided in the image display unit 302, thereby allowing the operator to designate a region of interest. This makes it easy to create an image having image quality requested by the operator.

Second Embodiment

In the second embodiment, a method of performing reconstructing processing and selection processing for two kinds of reconstructed images of an object will be described. A method of obtaining reconstructed images by individually acquiring and reconstructing left and right breasts will be explained. The arrangement and basic operation of an image reconstructing apparatus are the same as in the first embodiment and a description thereof will be omitted. A reconstructed image display method and an image selection method which are different from those in the first embodiment will be described.

Figure 6:
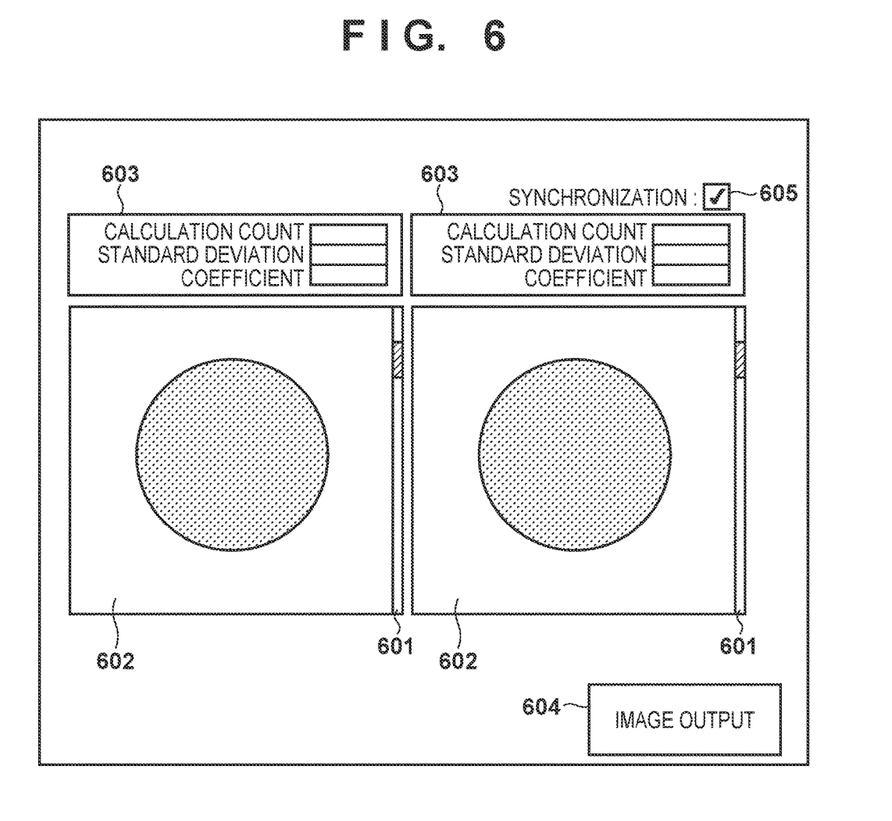
FIG. 6 is a schematic view showing an example of an image selection unit 600.

FIG. 6 is a schematic view showing an example of display of an image selection unit 600 according to this embodiment. Assume that reconstructed images obtained by individually, sequentially reconstructing left and right breasts in the same method as in the first embodiment have been input to the image selection unit 600.

The image selection unit 600 includes image selection instruction units 601, image display units 602, reconstruction information display units 603, an image output instruction unit 604, and a synchronization instruction unit 605. Each image selection instruction unit 601 serves as an interface used by the operator to select and instruct a reconstructed image. There are provided two image selection instruction units 601 including a combination of two arrow buttons and a slide bar according to this embodiment. The roles and arrangement of the respective arrow buttons and slide bar are the same as in the first embodiment and a description thereof will be omitted. This allows the operator to select reconstructed images with different calculation counts as left and right reconstructed images.

The synchronization instruction unit 605 serves as an interface used by the operator to instruct whether to perform selection and display processes of the left and right reconstructed images in synchronism with each other. The synchronization instruction unit 605 according to this embodiment includes a checkbox. If the checkbox is checked, left and right reconstructed images are selected in synchronism with each other. When one of the two image selection instruction units 601 is operated, images with the same calculation count are simultaneously selected as two kinds of reconstructed images. By selecting left and right images in synchronism with each other, the operator can readily obtain, by one operation, images having undergone the same number of calculation operations.

Note that as described in the first embodiment and the second modification, if the reconstructed images to be selected are obtained by the method of extracting an image for each change amount in predetermined coefficient, the method of extracting an image for each change amount in standard deviation of the pixel values of a predetermined image, or the like, the images having the same ordinal number of extraction are simultaneously selected. An arrangement of selecting and displaying, in synchronism with each other, images whose feature values such as standard deviations are almost equal to each other may be adopted. This makes it possible to simultaneously select images whose objective indices are equal to each other, thereby further facilitating image selection.

The image display units 602 display the reconstructed images selected by the image selection instruction units 601, respectively. In this example, the image display units 602 display the left and right images, respectively. That is, the image display units 602 simultaneously display the reconstructed images for each object. If the checkbox of the synchronization instruction unit 605 has been checked, an operation for changing the contrast and luminance of each display image, enlarged/reduced display, or the like is accepted, and the image display units 602 perform contrast and luminance adjustment, display magnification adjustment, slice position adjustment, slice selection, or the like in accordance with an operator instruction in synchronism with each other. The reconstruction information display units 603 display the pieces of information of the reconstructed images selected by the image selection instruction units 601, and display the pieces of information of both the left and right images. The image output instruction unit 604 serves as a user interface used by the operator to instruct to output the reconstructed images selected by the image selection instruction units 601.

Using the image selection unit 600 allows the operator to readily select a plurality of kinds of images associated with each other. Note that the method of selecting and outputting the reconstructed images of the left and right breasts has been explained in this embodiment. However, the present invention is not limited to this, and this embodiment is applicable when different reconstructed images are simultaneously displayed and selected. For example, the embodiment is usable as a method of selecting images of the same object or portion output under different image processing conditions. The image processing conditions indicate the pixel size of the reconstructed image, the slice thickness, the pixel size of a projection image, and the like. For example, the embodiment may be used as a method of selecting two kinds of reconstructed images output under the image processing conditions for outputting a high-resolution image having a small pixel size of the reconstructed image and a small slice thickness and the image processing conditions for outputting a low-noise image having a large pixel size and a large slice thickness. This makes it easy to select a plurality of kinds of images for different applications.

Third Embodiment

In the third embodiment, a method of performing reconstructing processing and selection processing for two kinds of reconstructed images will be described. In this embodiment, the arrangement and basic operation of an image reconstructing apparatus are the same as in the first embodiment and a description thereof will be omitted. A reconstructed image selection/output method different from that in the first embodiment will be described. To obtain reconstructed images by individually acquiring and reconstructing left and right breasts, reconstructing processing is performed for the left breast, a reconstructed image to be output is selected, and then reconstructing processing of the right breast is performed in accordance with the reconstruction information of the selected image.

Figure 7:
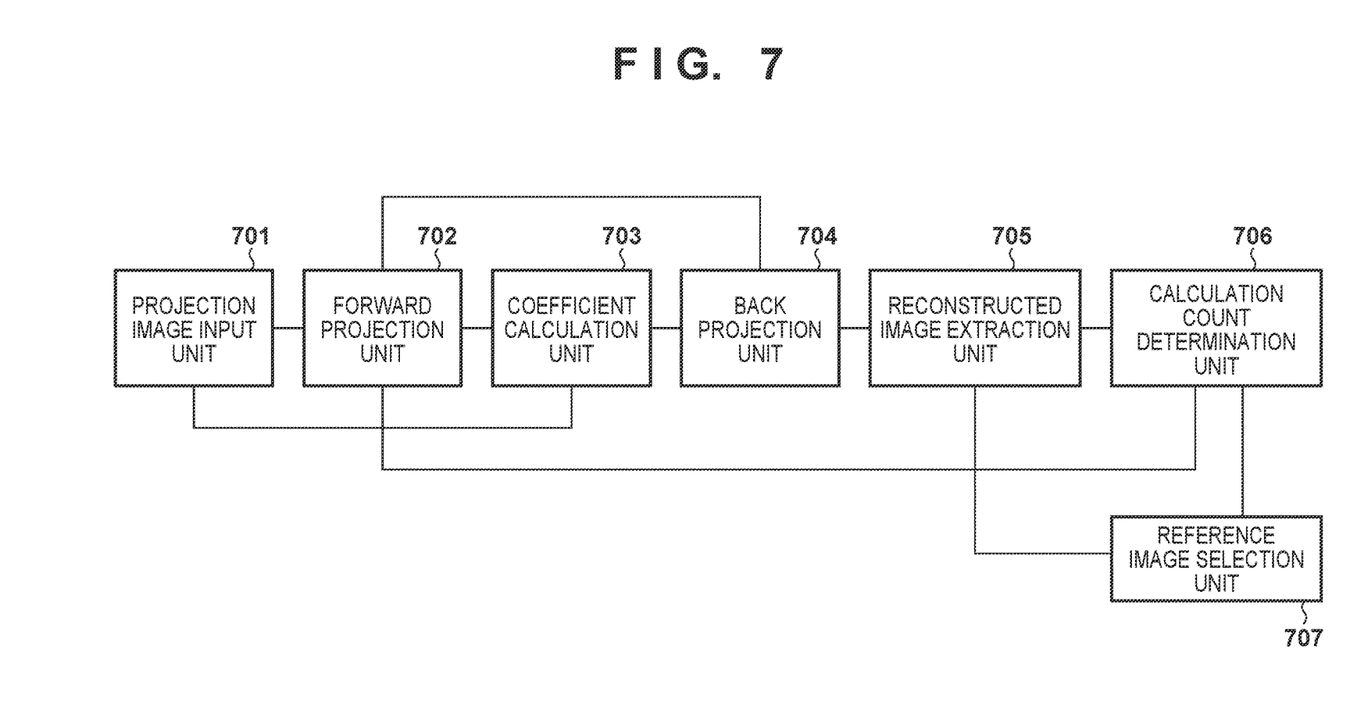
FIG. 7 is a block diagram showing the arrangement of an image reconstructing apparatus 700.

The arrangement of an image reconstructing apparatus 700 will be described with reference to FIG. 7. FIG. 7 is a block diagram showing the arrangement of the image reconstructing apparatus 700 according to this embodiment. As shown in FIG. 7, the image reconstructing apparatus includes a projection image input unit 701, a forward projection unit 702, a coefficient calculation unit 703, a back projection unit 704, a reconstructed image extraction unit 705, a calculation count determination unit 706, and a reference image selection unit 707.

Figure 8:
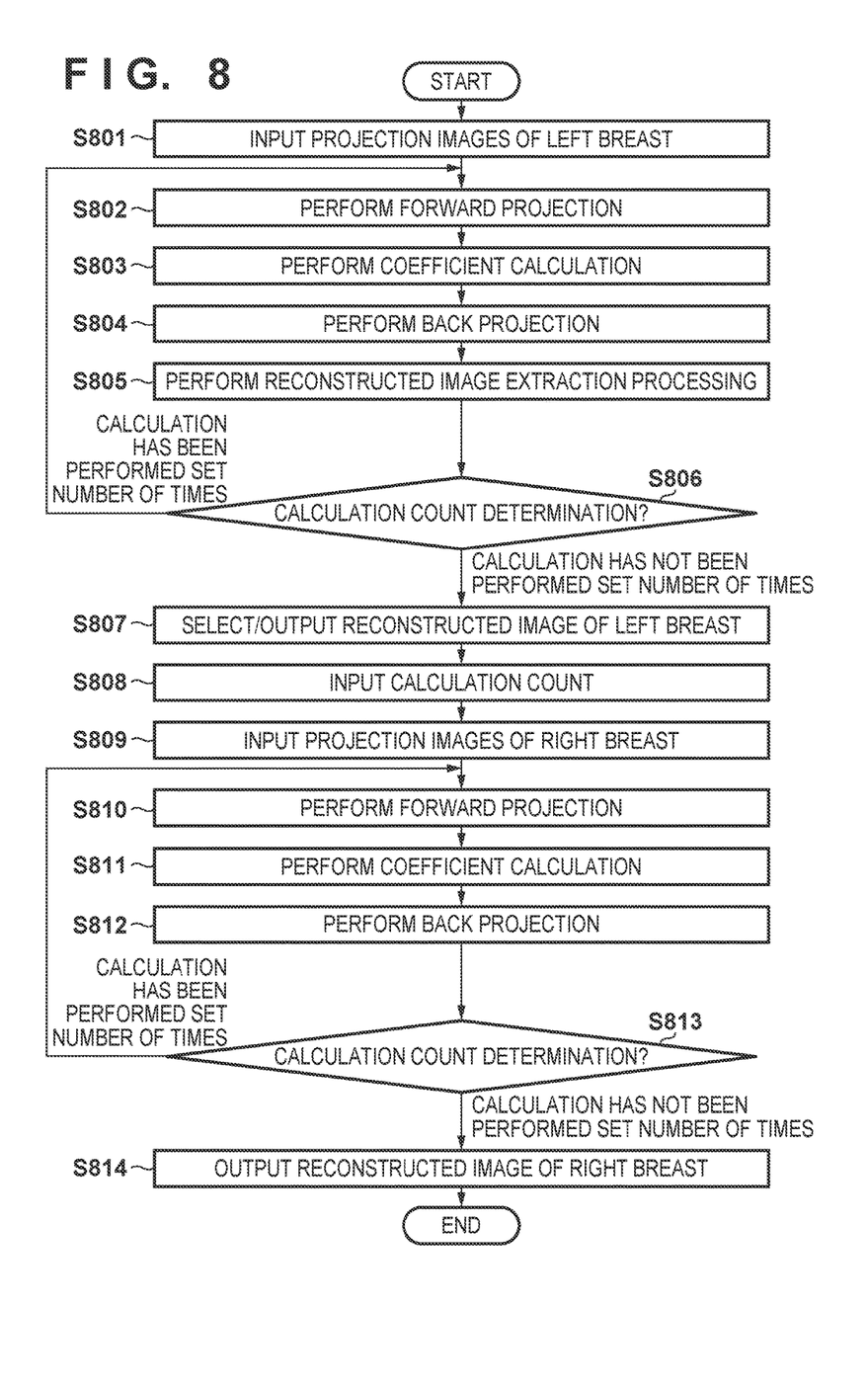
FIG. 8 is a flowchart illustrating a processing procedure executed by the image reconstructing apparatus 700.

The operation of the above-described image reconstructing apparatus 700 will be described with reference to FIG. 8. FIG. 8 is a flowchart illustrating a processing procedure executed by the image reconstructing apparatus 700 according to this embodiment. In steps S801 to S807, reconstructing processing is performed using acquired images of the left breast and a reconstructed image as a reference is selected. Operations in steps S801 to S806 are the same as in the first embodiment and a description thereof will be omitted. In step S807, the operator uses the reference image selection unit 707 to select a reconstructed image requested by the operator, and the reference image selection unit 707 outputs the selected reconstructed image. In step S808, the calculation count of the reconstructed image as a reference is input to the calculation count determination unit 706. In step S809, the projection image input unit 701 receives projection images obtained by acquiring the right breast from different angles by an imaging apparatus (not shown), and outputs them to the coefficient calculation unit 703.

In step S810, the forward projection unit 702 receives a reconstructed image, and creates a forward projection image. Note that if the calculation count is one, a reconstructed image containing an appropriate value other than 0 is input to the forward projection unit 702. In step S811, the coefficient calculation unit 703 compares the forward projection image with the projection image, thereby performing coefficient calculation. In step S812, the back projection unit 704 creates and updates the reconstructed image based on the reconstructed image and a coefficient.

In step S813, the calculation count determination unit 706 determines whether calculation has been performed the number of times input in step S808. If the calculation has not been performed the number of times, the reconstructed image created by the back projection unit 704 is output to the forward projection unit 702, and the process returns to step S810. If it is determined in step S813 that calculation has been performed the number of times, the reconstructed image of the right breast is output, thereby terminating the processing.

By performing the processes in steps S801 to S813 as described above, the operator can efficiently acquire another reconstructed image by using the first selected reconstructed image as a reference.

Note that this embodiment has exemplified an example in which the calculation counts of the reconstructed images of the left and right breasts are equalized. The present invention, however, is not limited to this. For example, a method of equalizing the feature values of images such as the standard deviations of images or the like may be used. This makes it easy to obtain an image with image quality equal to that of a reference image.

Note that this embodiment has described the method of selecting and outputting the reconstructed images of the left and right breasts. However, the present invention is not limited to this, and is applicable when a plurality of reconstructed images are output. For example, this embodiment is also usable, for example, when a reconstructed image of one subject is used as a reference to output reconstructed images of the subject, which are subsequently reconstructed, and when a reconstructed image obtained by acquiring and reconstructing a simulated phantom which is not human body data is used as a reference to output a reconstructed image of an actual subject.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-259276, filed Dec. 22, 2014, which is hereby incorporated by reference herein in its entirety.

What is claimed is:

1. An image reconstructing apparatus comprising:
a creation unit configured to create a reconstructed image for every calculation operation by performing predetermined repetitive calculation by iterative reconstruction for a plurality of images obtained by acquiring an object from different angles;
an extraction unit configured to extract at least one reconstructed image under a predetermined condition from the reconstructed images created by the creation unit;
a selection unit configured to display on a display unit information corresponding to the reconstructed images extracted by the extraction unit and information corresponding to the extracted reconstructed image, and to select at least one reconstructed image in accordance with an instruction of an operator on the display unit; and
an output unit configured to output the at least one reconstructed image selected by the selection unit.

2. The apparatus according to claim 1, wherein
the extraction unit extracts the at least one reconstructed image based on a calculation count of the repetitive calculation, and
the selection unit displays, on the display unit, the calculation count corresponding to the reconstructed image extracted by the extraction unit.

3. The apparatus according to claim 1, wherein
the extraction unit extracts the at least one reconstructed image based on a feature of each of the reconstructed images created by the creation unit, and
the selection unit displays, on the display unit, the feature corresponding to the reconstructed image extracted by the extraction unit.

4. The apparatus according to claim 3, wherein the feature is a feature within a specific range of each of the reconstructed images created by the creation unit.

5. The apparatus according to claim 3, wherein the feature includes a standard deviation of pixel values of each of the reconstructed images created by the creation unit.

6. The apparatus according to claim 3, wherein the feature includes an average value of absolute values of differences between pixels of an image before the repetitive calculation and pixels of a forward projection image obtained at a creation stage of each of the reconstructed images created by the creation unit.

7. The apparatus according to claim 1, wherein
the extraction unit extracts the at least one reconstructed image based on a coefficient obtained by comparing the image before the repetitive calculation and the forward projection image obtained at a creation stage of each of the reconstructed images created by the creation unit, and
the selection unit displays, on the display unit, the coefficient corresponding to the reconstructed image extracted by the extraction unit.

8. The apparatus according to claim 1, wherein the selection unit simultaneously displays, on the display unit, the plurality of reconstructed images extracted by the extraction unit and pieces of information corresponding to the extracted reconstructed images.

9. The apparatus according to claim 1, wherein if there are a plurality of objects, the selection unit simultaneously displays, for each of the objects, on the display unit, the reconstructed images extracted by the extraction unit and pieces of information corresponding to the extracted reconstructed images.

10. The apparatus according to claim 9, wherein in synchronism with information corresponding to one of the reconstructed images extracted by the extraction unit, the selection unit displays, on the display unit, another one of the reconstructed images extracted by the extraction unit.

11. The apparatus according to claim 1, wherein if there are a plurality of objects, a reconstructed image created for one of the plurality of objects is used as a reference to create another reconstructed image.

12. An image reconstructing method comprising:
creating a reconstructed image for every calculation operation by performing predetermined repetitive calculation by iterative reconstruction for a plurality of images obtained by acquiring an object from different angles;

extracting at least one reconstructed image under a predetermined condition from the reconstructed images created in the creating;

selecting at least one reconstructed image in accordance with an instruction of an operator on a display unit by displaying, on the display unit, the reconstructed image extracted in the extracting and information corresponding to the extracted reconstructed image; and outputting the at least one reconstructed image selected in the selecting.

13. A non-transitory computer-readable storage medium storing a computer program for causing a computer to execute a method of an image reconstructing apparatus, the method comprising:

creating a reconstructed image for every calculation operation by performing predetermined repetitive calculation by iterative reconstruction for a plurality of images obtained by acquiring an object from different angles;

extracting at least one reconstructed image under a predetermined condition from the reconstructed images created in the creating;

selecting at least one reconstructed image in accordance with an instruction of an operator on a display unit by displaying, on the display unit, the reconstructed image extracted in the extracting and information corresponding to the extracted reconstructed image; and outputting the at least one reconstructed image selected in the selecting.

\* \* \* \* \*